United States Patent
Huang et al.

(10) Patent No.: US 11,464,823 B2
(45) Date of Patent: Oct. 11, 2022

(54) CURCUMIN CARBON QUANTUM DOTS AND USE THEREOF

(71) Applicant: Chih-Ching Huang, Keelung (TW)

(72) Inventors: Chih-Ching Huang, Keelung (TW); Chin-Jung Lin, Taipei (TW); Shiow-Yi Chen, Taipei (TW); Lung Chang, Taipei (TW); Han-Jia Lin, Taipei (TW)

(73) Assignee: Chih-Ching Huang, Keelung (TW)

( * ) Notice: Subject to any disclaimer, the term of this patent is extended or adjusted under 35 U.S.C. 154(b) by 293 days.

(21) Appl. No.: 16/623,774

(22) PCT Filed: Jun. 6, 2018

(86) PCT No.: PCT/CN2018/090030
§ 371 (c)(1),
(2) Date: Dec. 18, 2019

(87) PCT Pub. No.: WO2019/232701
PCT Pub. Date: Dec. 12, 2019

(65) Prior Publication Data
US 2020/0138896 A1 May 7, 2020

(51) Int. Cl.
*A61K 36/9066* (2006.01)
*A61K 9/14* (2006.01)
*A61P 31/12* (2006.01)
*B82Y 5/00* (2011.01)
*B82Y 15/00* (2011.01)
*B82Y 30/00* (2011.01)
*B82Y 40/00* (2011.01)

(52) U.S. Cl.
CPC ............ *A61K 36/9066* (2013.01); *A61K 9/14* (2013.01); *A61P 31/12* (2018.01); *B82Y 5/00* (2013.01); *B82Y 15/00* (2013.01); *B82Y 30/00* (2013.01); *B82Y 40/00* (2013.01)

(58) Field of Classification Search
None
See application file for complete search history.

(56) References Cited

FOREIGN PATENT DOCUMENTS

| JP | 2018035035 A | * | 3/2018 |
|----|---|---|---|
| JP | 2018035035 A | | 3/2018 |

OTHER PUBLICATIONS

Yang, X.X., et al., Curcumin modified silver nanoparticles for highly efficient inhibition of respiratory syncytial virus infection, Nanoscale, Jan. 6, 2016, on Dec. 18, 2019 IDS.*
Chun, S., et al., The ethanopharmacological aspect of carbon nanodots in turmeric smoke, Sci. Rep. 6 (2016) 35586-35597).*
Kazufumi et al., Curcumin Prevents Replication of Respiratory Syncytial Virus and the Epithelial Responses to it in Human Nasal Epithelial Cells, Plos One, Sep. 18, 2013, pp. 1-14, vol. 8, Issue 9, e70225.*
JP 2018035035 A, Description, English machine translation (Espacenet).*
Leonardo Padilla-S et al., Inhibitory Effects of Curcumin on Dengue Virus Type 2-infected Cells in Vitro, Arch Virol (2014), Oct. 1, 2013, pp. 573-579, Springer.
Sebla B. Kutluay et al., Curcumin Inhibits Herpes Simplex Virus Immediate-early Gene Expression by a Mechanism Independent of p300/CBP Histone Acetyltransferase Activity, Virology 373 (2008), Jan. 14, 2008, pp. 239-247, ELSEVIER.
Abhijit Mazumder et al., Inhibition of Human Immunodeficiency Virus Type-1 Integrase by Curcumin, Biochemical Pharmacology, 1995, pp. 1165-1170, vol. 49, No. 8, Elsevier Science Ltd, Great Britain.
Kazufumi Obata et el., Curcumin Prevents Replication of Respiratory Syncytial Virus and the Epithelial Responses to It in Human Nasal Epithelial Cells, PLOS ONE, Sep. 18, 2013, pp. 1-14, vol. 8, Issue 9, e70225.
Reetha Anand et al., Bioavailability of Curcumin: Problems and Promises, Molecular Pharmaceutics, Nov. 14, 2007, pp. 807-818, vol. 4, No. 6, American Chemical Society.
Yongqiang Dong et al., Blue Luminescent Graphene Quantum Dots and Graphene Oxide Prepared by Tuning the Carbonization Degree of Citric Acid, Carbon 50 (2012), Jun. 14, 2012, pp. 4738-4743, ELSEVIER.
Hong-Jyuan Jian et al., Super-Cationic Carbon Quantum Dots Synthesized from Spermidine as an Eye Drop Formulation for Topical Treatment of Bacterial Keratitis, ACS Nano 2017, Jul. 5, 2017, pp. 6703-6716, vol. 11, American Chemical Society.
Xiao Xi Yang et al., Curcumin Modified Silver Nanoparticles for Highly Efficient Inhibition of Respiratory Syncytial Virus Infection, Nanoscale, Jan. 6, 2016, cover page + pp. 1-9, The Royal Society of Chemistry.
Wenwen Dai et al., Antiviral Effects of Retro-2cycl and Retro-2.1 Against Enterovirus 71 in vitro and in vivo, Antiviral Research 144 (2017), Jul. 5, 2017, pp. 311-321, ELSEVIER.
International Search Report together with Written Opinion of the International Searching Authority of PCT Patent Application No. PCT/CN2018/090030 dated Mar. 6, 2019.

* cited by examiner

*Primary Examiner* — H. Sarah Park (57) ABSTRACT

An engineered nanoparticle having a curcumin carbon quantum dot and the use thereof for antiviral application are disclosed. A method of preparation of a curcumin carbon nanoparticle is also disclosed, the method comprises heating a curcumin powder at a temperature range from 120 to 210° C. to yield a residue; dissolving the residue with sodium phosphate buffer in a solution; and purifying the solution.

24 Claims, 12 Drawing Sheets

CURCUMIN CARBON QUANTUM DOTS AND USE THEREOF

FIELD OF THE INVENTION

The present invention relates to the area of nanoparticle engineering. More particularly, the present invention relates to an engineered nanoparticle having a curcumin carbon quantum dot and the use thereof for antiviral application. The present invention also relates to a method of preparation of a curcumin nanoparticle.

BACKGROUND OF THE INVENTION

Nanomaterials have many applications in human health area. One of that is the suppressive effect of nanoparticles on virus infection. The antiviral effect is achieved with nanoparticles such as gold nanoparticles, ZnO nanoparticles, carbon nanomaterials, nanoclay and silicon nanoparticles, modified by different functional molecules. The decorated nanoparticles can inactivate the virus directly or block viral entry into cells by interfering the recognition of the receptors on the host cells surface. The smaller size of the nanoparticles has the more inhibitory effects due to larger specific surface areas interacted with viral envelope proteins directly. Moreover, the small nanoparticles can enter into the host cell easily and interact with the viral genome and/or enzymes to interfering the viral replication.

Curcumin, a component of turmeric, has been described to have several functions in preventing or treating diseases, such as cancers and viral infections. Previous works have demonstrated that curcumin is an effectively antiviral compound against diverse viruses such as dengue virus (serotype 2) (Padilla-S et al., 2013), herpes simplex virus (Kutluay et al., 2008), human immunodeficiency virus (Mazumder et al., 1995), and so on. Recently, Kojima's group reported that curcumin could prevent replication and budding of respiratory syncytial virus (RSV) (Obata et al., 2013).

The poor solubility in water and low bioavailability of curcumin greatly limit its applicable range in clinics (Anand et al., 2007). In recent research, the combination of both curcumin and silver nanoparticles (AgNPs) can interfere the interaction between respiratory syncytial virus (RSV) and the host cells, and block viral entry into cells. Given the abundance of curcumin and its prevalence in the human diet, the combination of curcumin and nanoparticle provides effective and safe new prophylaxis and treatment of viral infection.

SUMMARY OF THE INVENTION

The present invention provides to a method of preparation of a curcumin nanoparticle, comprises the steps of heating a curcumin powder at a temperature range from 120 to 210° C. to yield a residue; dissolving the residue with sodium phosphate buffer in a solution; and purifying the solution.

According to the above, wherein the temperature is 180° C.

According to the above, further comprises the step of homogenizing the solution.

According to the above, wherein the step of purifying the solution is performed in sodium chloride solution through a dialysis membrane.

In one aspect, the invention provides an engineered nanoparticle prepared by a method including the steps of heating a curcumin powder at a temperature range from 120 to 210° C. to yield a residue; dissolving the residue with sodium phosphate buffer in a solution; and purifying the solution comprises at least one curcumin carbon quantum dot.

According to the above, wherein the curcumin carbon quantum dot is uniform, monodispersed sphere.

According to the above, wherein the curcumin carbon quantum dot has a diameter of 5.4 to 7.0 nm.

In one aspect, the invention provides an engineered nanoparticle comprises at least one curcumin carbon quantum dot.

According to the above, wherein the curcumin carbon quantum dot is uniform, monodispersed sphere.

According to the above, wherein the curcumin carbon quantum dot has a diameter of 5.4 to 7.0 nm.

In one aspect, the invention provides a composition having an antiviral activity comprises an effective amount of an engineered nanoparticle having at least one curcumin carbon quantum dot.

According to the above, wherein the curcumin carbon quantum dot is uniform, monodispersed sphere.

According to the above, wherein the curcumin carbon quantum dot has a diameter of 5.4 to 7.0 nm.

In one aspect, the invention provides a method of preparing an antiviral composition, comprising the steps of heating a curcumin powder at a temperature range from 120 to 210° C. to yield a residue; dissolving the residue with sodium phosphate buffer in a solution; and purifying the solution.

According to the above, wherein the temperature is 180° C.

According to the above, further comprises the step of homogenizing the solution.

According to the above, wherein the step of purifying the solution is performed in sodium chloride solution through a dialysis membrane.

In one aspect, the invention provides a method for treatment of an infection, condition or disorder caused by a virus, comprising administering a therapeutically effective amount of an engineered nanoparticle composition having at least one curcumin carbon quantum dot.

According to the above, wherein the virus is selected from a group consisting of Enterovirus.

According to the above, wherein the curcumin carbon quantum dot is uniform, monodispersed sphere.

According to the above, wherein the curcumin carbon quantum dot has a diameter of 5.4 to 7.0 nm.

The foregoing and other features and advantages of the present invention disclosure will be more readily appreciated by one of ordinary skilled in the art from the following figures, embodiments and descriptions.

DETAIL DESCRIPTION OF THE INVENTION

Disclosed in detail herein are methods, structures and compostitions for providing a curcumin carbon quantum dots and use thereof. The invention will be able to be practiced by one skilled in the art that references to the following embodiments and descriptions.

Synthesis of Curcumin Carbon Quantum Dots

Curcumin carbon quantum dots (hereafter referred as "Cur-CQDs") were synthesized using a simple heating method. For example, 50 mg of curcumin powder were placed in a 20 mL beaker and heated in a muffle furnace at 120-210° C. for 2 hours to yield the dark brown residues. The residues were cooled to room temperature (25° C.) and dissolved in sodium phosphate buffer (200 mM, 5 mL, pH 12). This solution was sonicated for 1 hour and subsequently centrifuged at a relative centrifugal force (RCF) of 35,000 g for 1 hour to remove large particles. The brownish yellow supernatant was diluted with DI water to a final volume of 18 mL and then dialyzed in sodium chloride solution (10 mM, ~2 L) through a dialysis membrane (MWCO=0.5-1 kD, Float-A-Lyzer G2, Spectrum Laboratories, Rancho Dominguez, Calif., USA) for 5 hours. The sodium chloride solution was replaced every 1 hour. After 5 hours, sodium chloride solution was replaced with ultrapure water and dialyzed for 18 hours. Ultrapure water was replaced every 6 hours. The purified Cur-CQDs solution was stored at 4° C. when not in use. The concentration of the purified CQDcurs in the solution (in terms of mg mL$^{-1}$) was determined by freeze drying method.

Characterization of Cur-CQDs

I. Sizes

HRTEM (High Resolution Transmission Electron Microscopy) images of CQDcurs are obtained by using a field emission gun transmission electron microscopy (FE-TEM, Tecnai F20 G2, FEI, USA).

Figure 1:
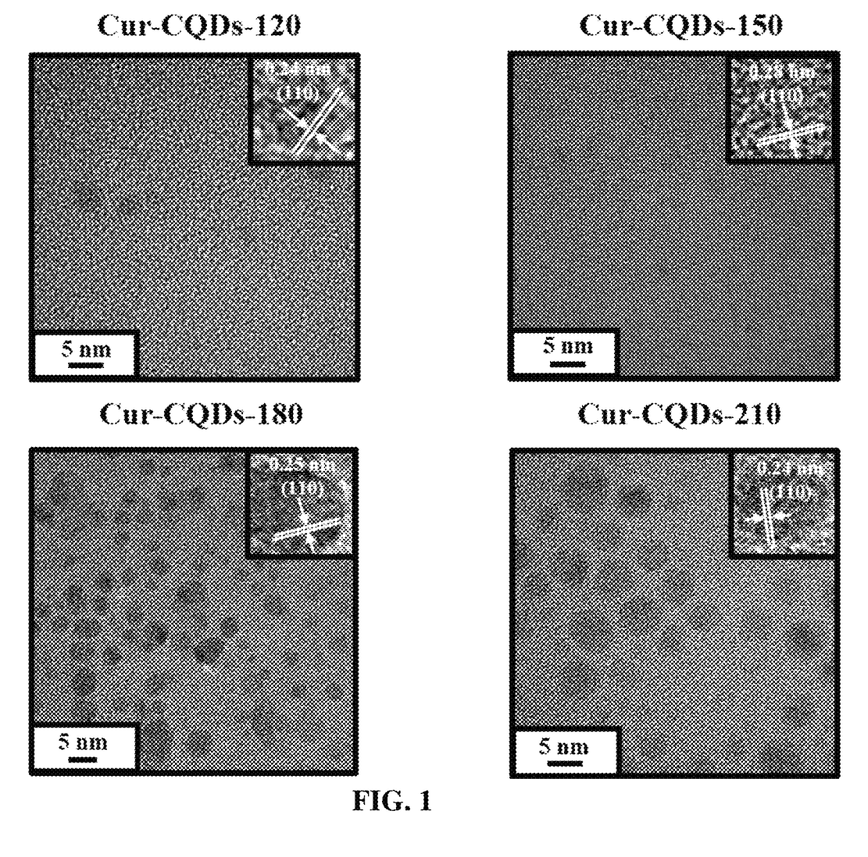
FIG. 1 shows high-resolution transmission electron microscopy (HRTEM) image of curcumin carbon quantum dots (Cur-CQDs) synthesized at 120, 150, 180 and 210° C.

In certain embodiments, the HRTEM image of Cur-CQDs synthesized at 120, 150, 180 and 210° C. (FIG. 1) shows that the as-prepared Cur-CQDs were uniform, monodispersed spheres with a mean diameter of 6.2±0.8 nm from 100 counts. The lattice structure (d-spacing: 0.24 nm; (112) plane) is discernible in the HRTEM image. The Cur-CQDs synthesized at the lower temperature have the less particles because of the lower yield.

II. Fluorescence and UV-Vis Absorption Spectra

Fluorescence and UV-Vis absorption spectra of as-prepared Cur-CQDs are recorded by using a monochromatic microplate spectrophotometer (Synergy 4 Multi-Mode; Biotek Instruments, Winooski, Vt., USA). Fluorescence spectra of the as-prepared Cur-CQDs in 5 mM sodium phosphate buffer (pH 7.4) are measured at an excitation wavelength of 365 nm.

Figure 2:
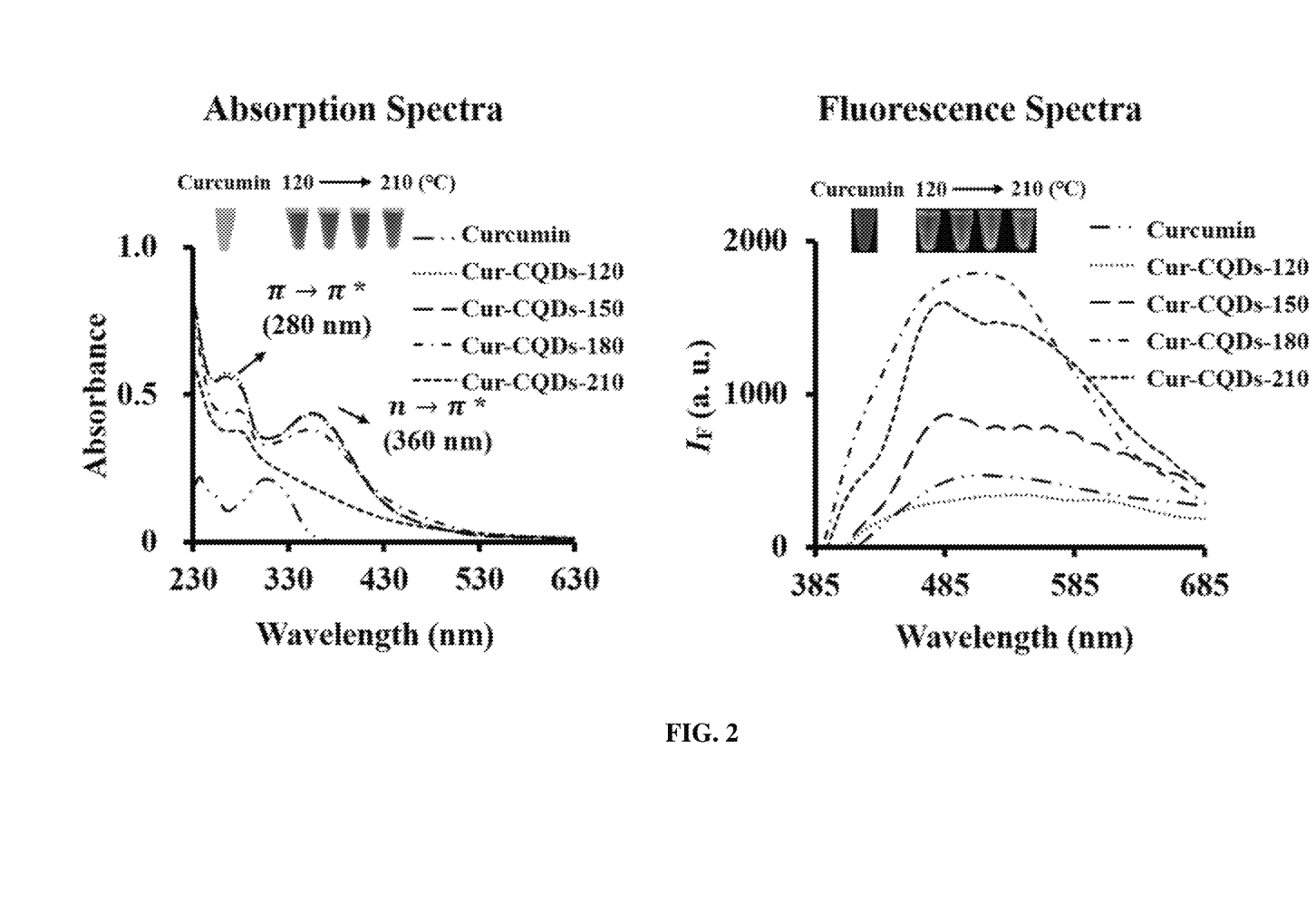
FIG. 2 shows fluorescence and UV-Vis absorption spectra of Cur-CQDs synthesized at 120, 150, 180 and 210° C.

FIG. 2 shows the fluorescence and UV-Vis absorption spectra of Cur-CQDs synthesized at 120, 150, 180 and 210° C. and photographs of the corresponding solutions (absorption spectra) before and (fluorescence spectra) after excitation with a UV lamp (365 nm).

In certain embodiments, fluorescence spectra of Cur-CQDs are recorded at excitation wavelength of 365 nm. The fluorescence intensities ($I_F$) are plotted in arbitrary units (au).

III. XRD Spectra

XRD is performed by using a multifunction high power X-ray diffractometer (XRD, D8 DISCOVER SSS, BRUKER, USA) with Al Kα X-ray radiation as the X-ray source for excitation. Binding energies are corrected by using the C 1s peak at 284.6 eV as the standard.

Figure 3:
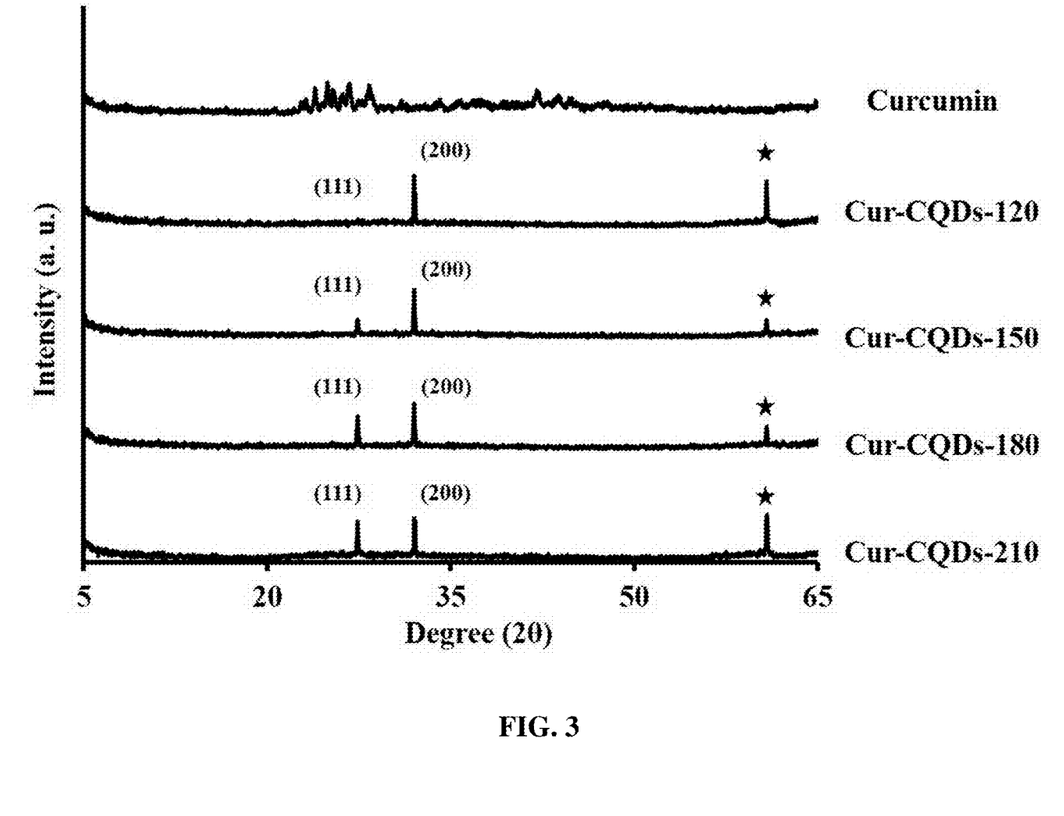
FIG. 3 shows the X-ray diffraction (XRD) spectra of Cur-CQDs synthesized at 120, 150, 180 and 210° C.

FIG. 3 shows the XRD Spectra of Cur-CQDs synthesized at 120, 150, 180 and 210° C.

In certain embodiments, the X-ray diffraction (XRD) pattern (002 plane) corresponds to the Cur-CQDs d-spacing of 0.24 nm.

IV. Elemental Analysis

Elemental analysis is performed by using an electron spectroscopy for chemical analysis PHI 5000 VersaProbe (Physical Electronics, USA) for N, C, H, O, and S.

Table. 1 shows the elemental analysis of Cur-CQDs synthesized at 120, 150, 180 and 210° C.

In certain embodiments, as reaction temperature increase, the carbon content of Cur-CQDs increase due to increased carbonization. In contrast, the oxygen content of Cur-CQDs decrease due to dehydration.

TABLE 1

Elemental analysis of curcumin and
Cur-CQDs synthesized at 120, 150, 180, and 210° C.
Elemental compositions[a]

|  | C (%) | O (%) | H (%) |
|---|---|---|---|
| Curcumin | 68.68 | 25.08 | 5.47 |
| Cur-CQDs-120 | 53.46 | 39.41 | 7.13 |
| Cur-CQDs-150 | 58.05 | 35.66 | 6.29 |
| Cur-CQDs-180 | 57.29 | 36.96 | 5.75 |
| Cur-CQDs-210 | 58.20 | 34.71 | 7.09 |

[a]Determined by elemental analysis.

V. FT-IR Spectra

FT-IR is performed by using a fourier transform infrared spectrometers (FTIR, FT/IR-6100, JASCO, USA).

Figure 4:
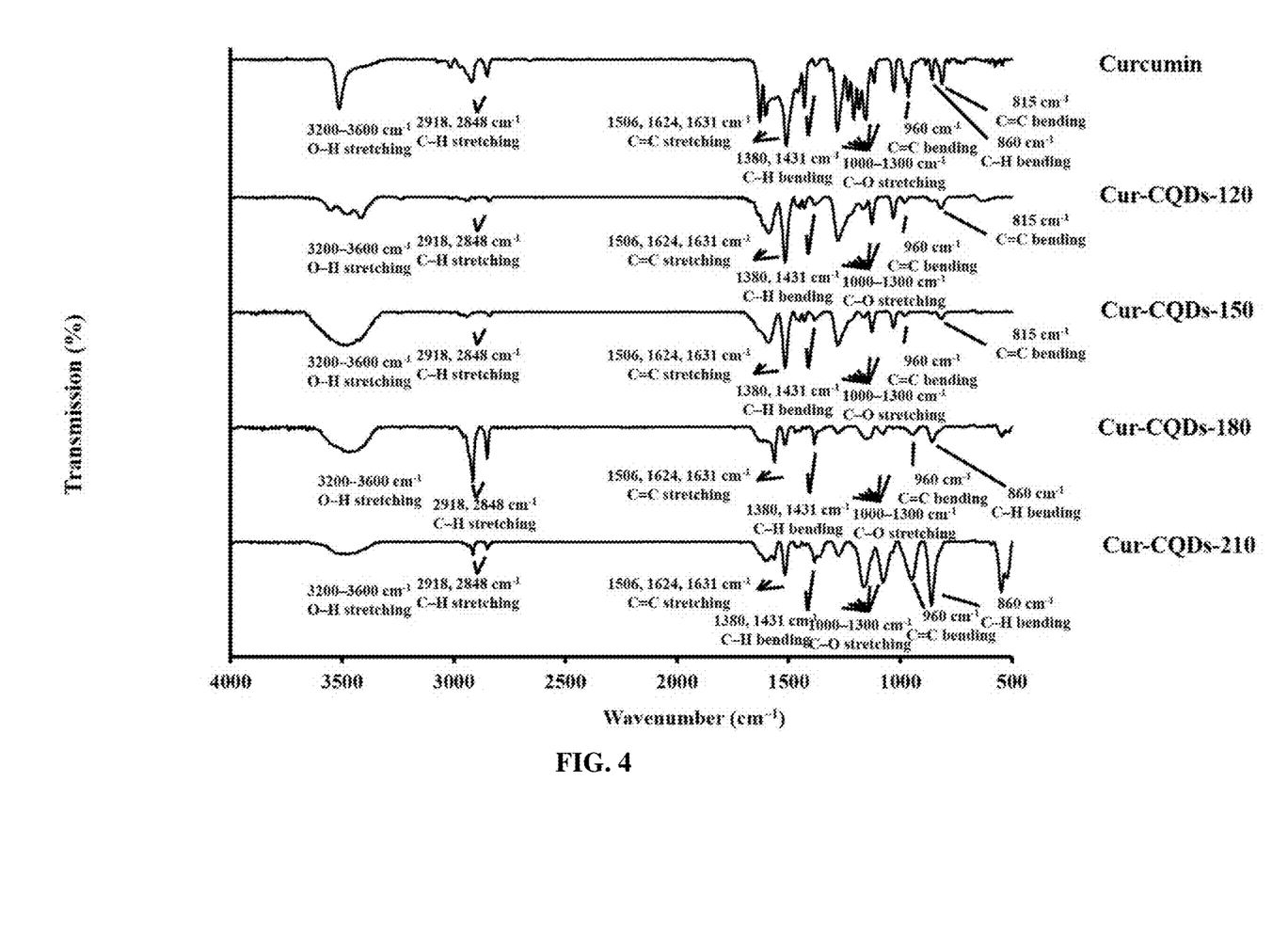
FIG. 4 shows the Fourier-transform infrared spectroscopy (FTIR) spectra of Cur-CQDs synthesized at 120, 150, 180 and 210° C.

FIG. 4 shows the FTIR Spectra of Cur-CQDs synthesized at 120, 150, 180 and 210° C.

In certain embodiments, the Cur-CQDs retain the curcumin functional groups even when the synthesized temperature increased up to 210° C.

VI. TGA and DSC Analysis

Temperature-dependent thermal gravimetric analyses (TGA) and differential scanning calorimetry (DSC) analysis are performed by using TA-Q500 (TA Instruments, New Castle, Del., USA) and Du Pont TA Instrument DSC-2010, respectively.

Figure 5:
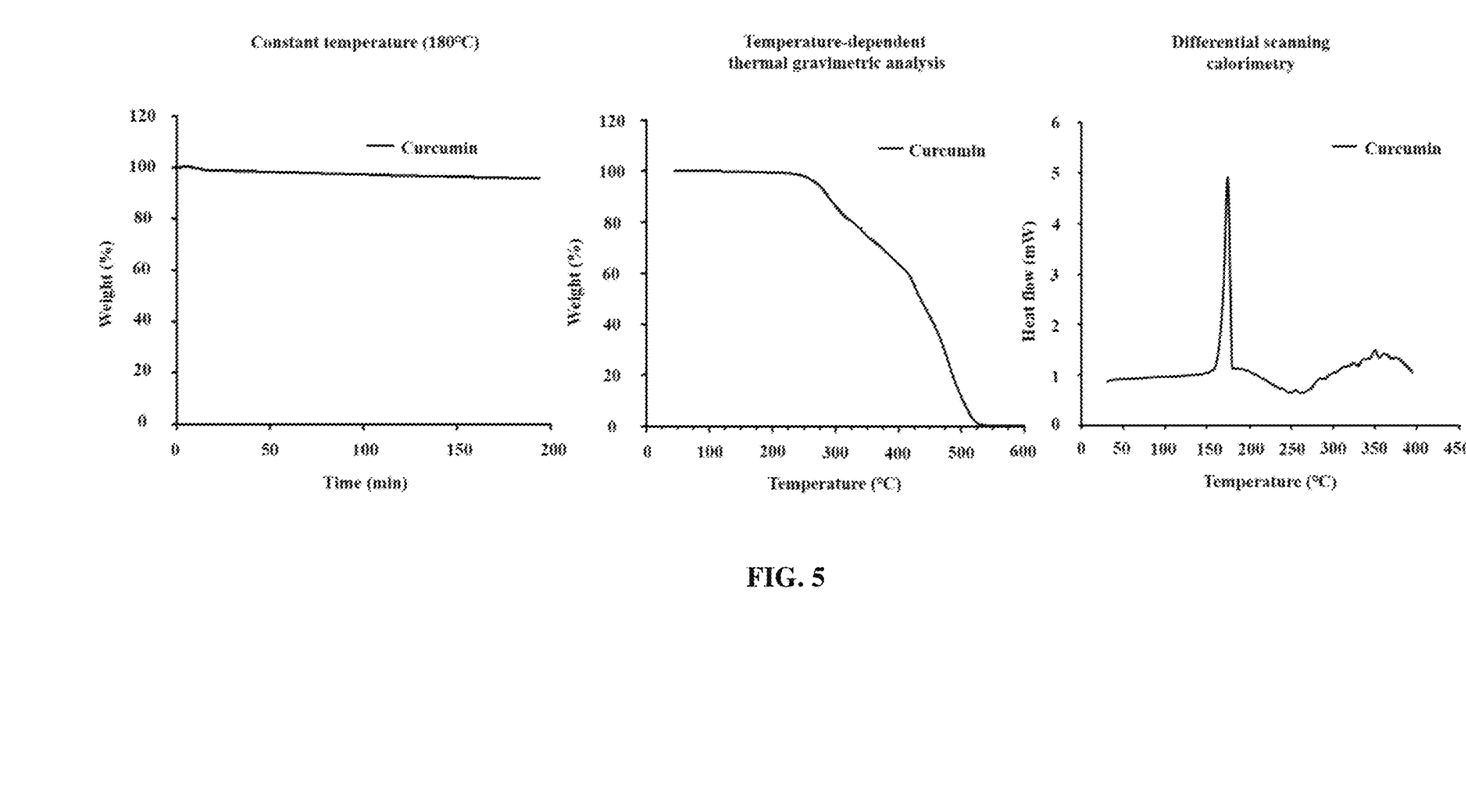
FIG. 5 shows the constant temperature (180° C.), temperature-dependent thermal gravimetric analyses, and differential scanning calorimetry of Cur-CQDs.

FIG. 5 shows the constant temperature (180° C.) and temperature-dependent TGA, and DSC spectra of as-prepared CQDcurs.

In certain embodiments, curcumin undergo melting, polymerization, carbonization-based nucleation, and growth to form stable Cur-CQDs at 180-210° C. The curcumin is easily over carbonization and/or decomposition cause a large dramatic weight lose when the temperature is higher than 270° C. DSC shows a melting (endothermic peak) and polymerization/carbonization (broaden exothermic band) at ~180° C. and 250° C., respectively.

Antiviral Activities of Cur-CQDs

I. The Cytopathic Effect (CPE) Result of Cur-CQDs

RD cells were seeded at $7.5 \times 10^3$ cells/well in 96-well plates and incubated for 24 hours at 37° C. To analyze how Cur-CQDs affect the infectivity of EV71, Cur-CQDs pre-treatment, post-treatment, co-treatment assay was taken as follows. For pre-treatment, Cur-CQDs were pre-incubated with RD cells at 37° C. for 24 hours and then cultured with EV71 for 48 hours at 37° C. For post-treatment, EV71 were pre-incubated with RD cells at 37° C. for 24 hours, after that, cell monolayers were washed with PBS to remove non-adherent virus and further incubated with DMEM (containing 2% FBS and Cur-CQDs) at 37° C. for 48 hours. For co-treatment, EV71 were pre-incubated with series of CQD-curs at 37° C. for 1 hour, then cultured with RD cells for 72 hours at 37° C. Negative (cells only) and positive (cells infected with EV71 without Cur-CQDs) controls were set as well. Cytopathic effect (CPE) was observed in inoculated cells on the third day.

Figure 6:
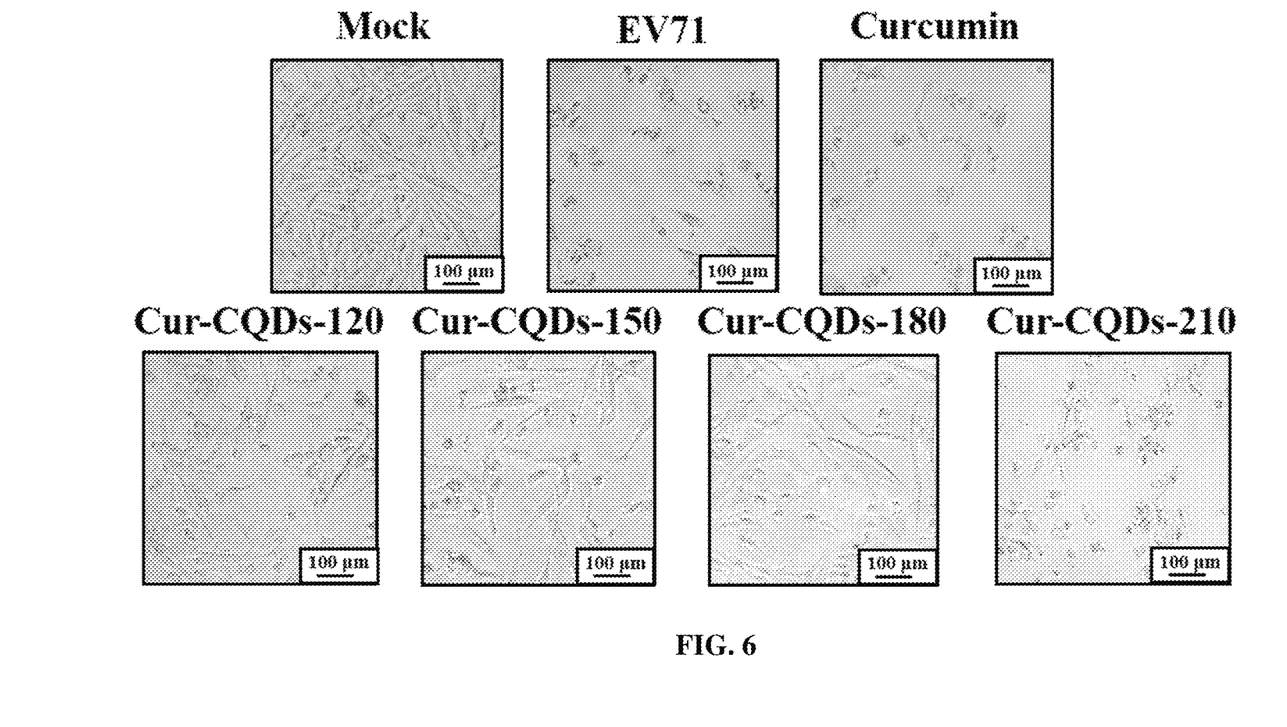
FIG. 6 shows the cytopathic effect (CPE) results of human rhabdomyosarcoma (RD) cells co-treated with EV71 virus and Cur-CQDs.

In certain embodiments, when the RD cells co-treated with EV71 virus and Cur-CQDs, the Cur-CQDs-180 have the best effect surpassing even curcumin (FIG. 6).

Figure 7:
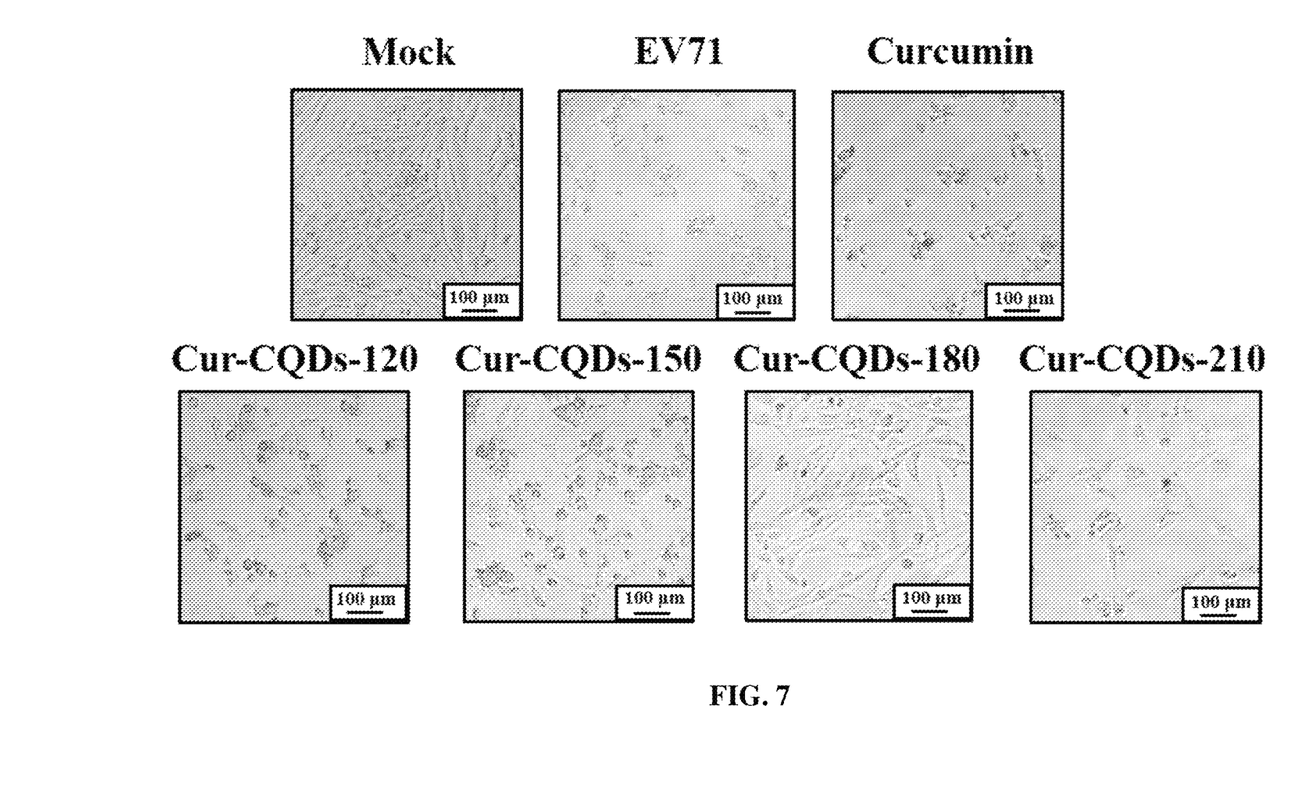
FIG. 7 shows the cytopathic effect (CPE) result of RD cells infected with EV71 virus then post-treated with Cur-CQDs.

In certain embodiments, when the RD cells infected with EV71 virus then post-treated with Cur-CQDs, the Cur-CQDs-180 have the best effect surpassing even curcumin (FIG. 7).

Figure 8:
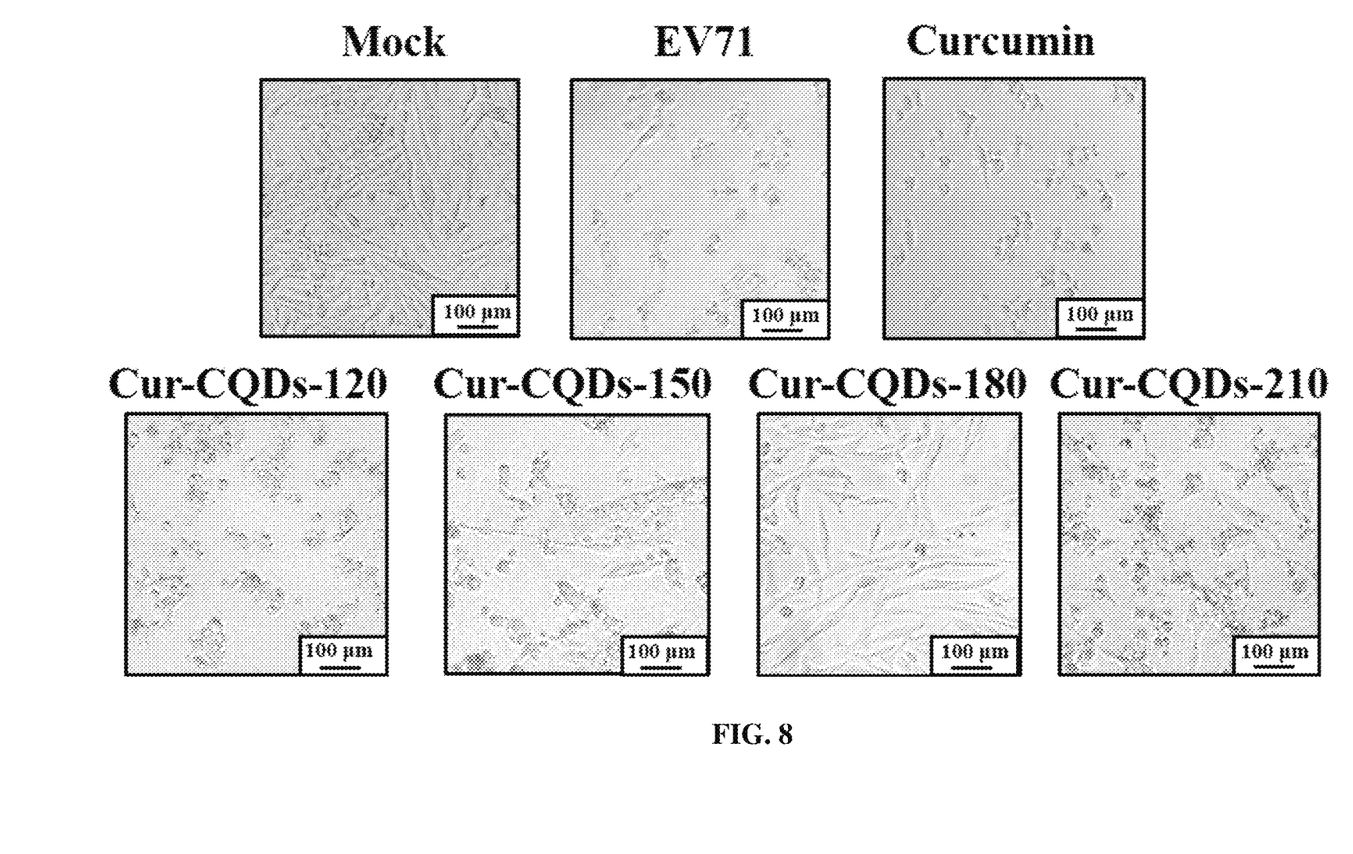
FIG. 8 shows the cytopathic effect (CPE) result of RD cells pre-treated with Cur-CQDs then infected with EV71 virus.

In certain embodiments, when the RD cells pre-treated with Cur-CQDs then infected with EV71 virus, the Cur-CQDs-180 have the best effect surpassing even curcumin (FIG. 8).

Figure 9:
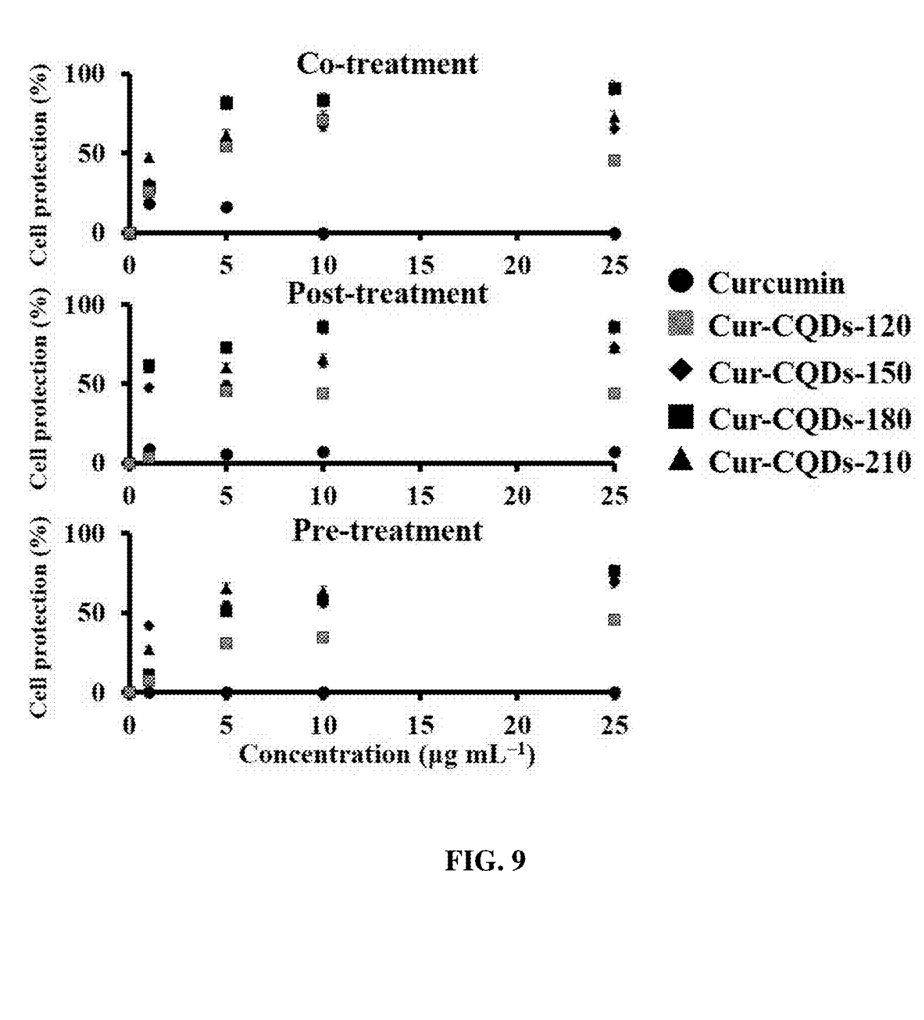
FIG. 9 shows antiviral activities of Cur-CQDs.

In certain embodiments, the Cur-CQDs-180 have the best effect surpassing even curcumin. Co-treatment have the best effect and with cell protection rate up to 90% (FIG. 9).

II. Cytotoxicity of Cur-CQDs

The in vitro cellular viability of the as-prepared Cur-CQDs was evaluated using the Presto blue. First, approximately $7.5 \times 10^3$ RD cells/well were seeded in 96-cell plates and were fed with DMEM containing 10% fetal bovine serum (FBS). After 24 hours of incubation in a humidified incubator with 5% $CO_2$ at 37° C., the medium was removed from each well, and RD cells were washed with phosphate buffered saline (PBS, pH 7.4). Then, sample solutions (Cur-CQDs with different concentrations) or the control solutions were added in and incubated with cells for 24 hours to 72 hours. Each concentration was tested with 4 sets of parallel samples. After that, the culture medium was replaced with Presto blue and incubated for another 1 hour at 37° C. Finally, fluorescence was measured at an excitation wavelength at 540 nm and an emission wavelength at 590 nm with a BioTek Microplate Reader. The viability of cells was expressed as the percentage of control untreated cells (100%).

Figure 10:
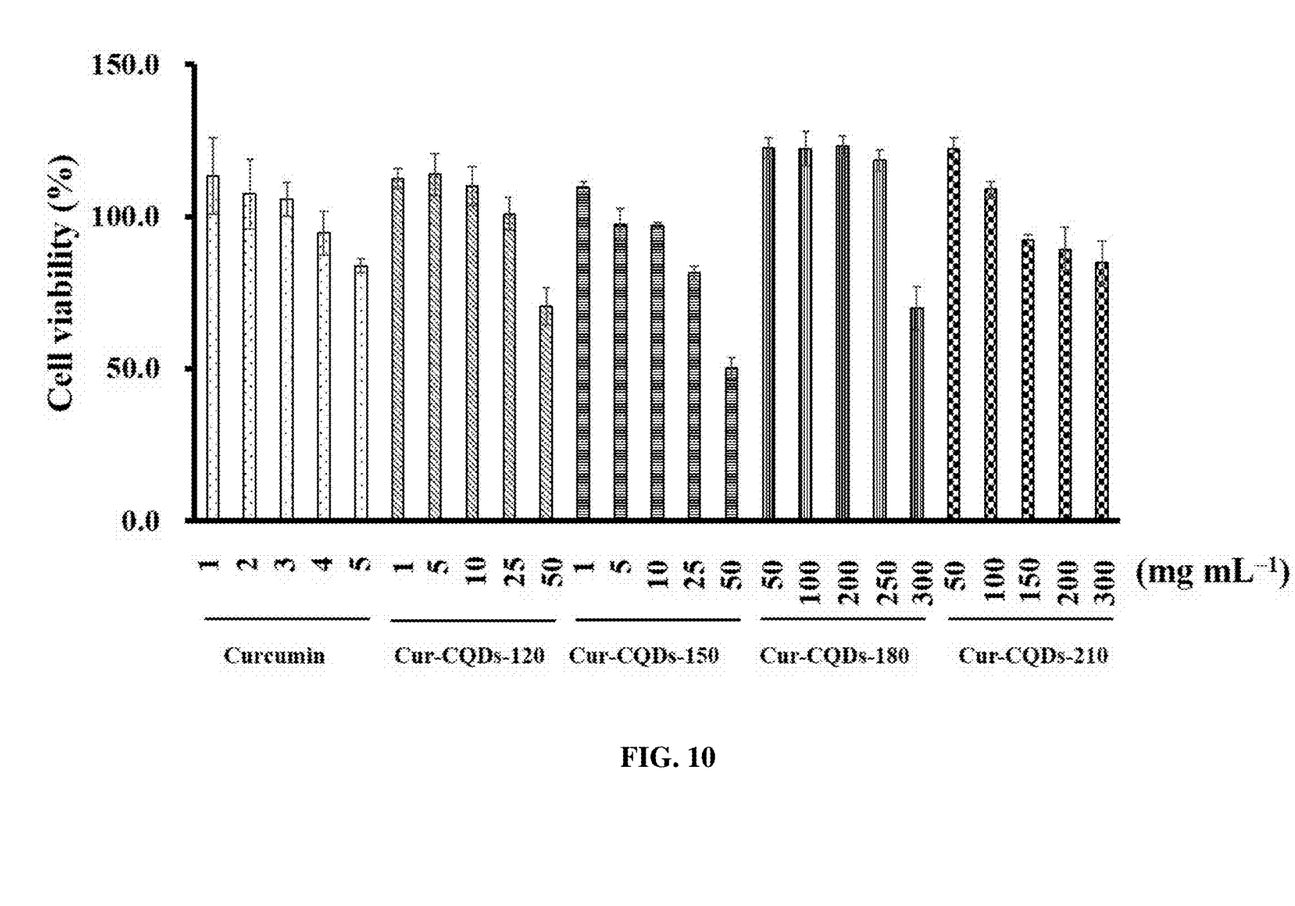
FIG. 10 shows the cell viability of Cur-CQDs.

In certain embodiments, the Cur-CQDs-180 shows better cell viability compared to curcumin with $CC_{50}$ of 452 mg $mL^{-1}$ (FIG. 10).

III. TCID50 of Cur-CQDs

The viral titer of EV71 was measured by using tissue culture infectious doses (TCID50) test. RD cell monolayers were seeded at $7.5 \times 10^3$ cells/well in 96-well plates, 24 hours before infection. Serial 10-fold dilutions of the separately collected EV71 were made in serum-free medium, and 0.1 mL was used to infect cells for 2 hours at 37° C. Virus was aspirated from each well, and the DMEM with 2% FBS was added. The plates were incubated at 37° C. with 5% $CO_2$ for 72 hours. The final value of TCID50 is calculated according to Reed-Muench formula.

Figure 11:
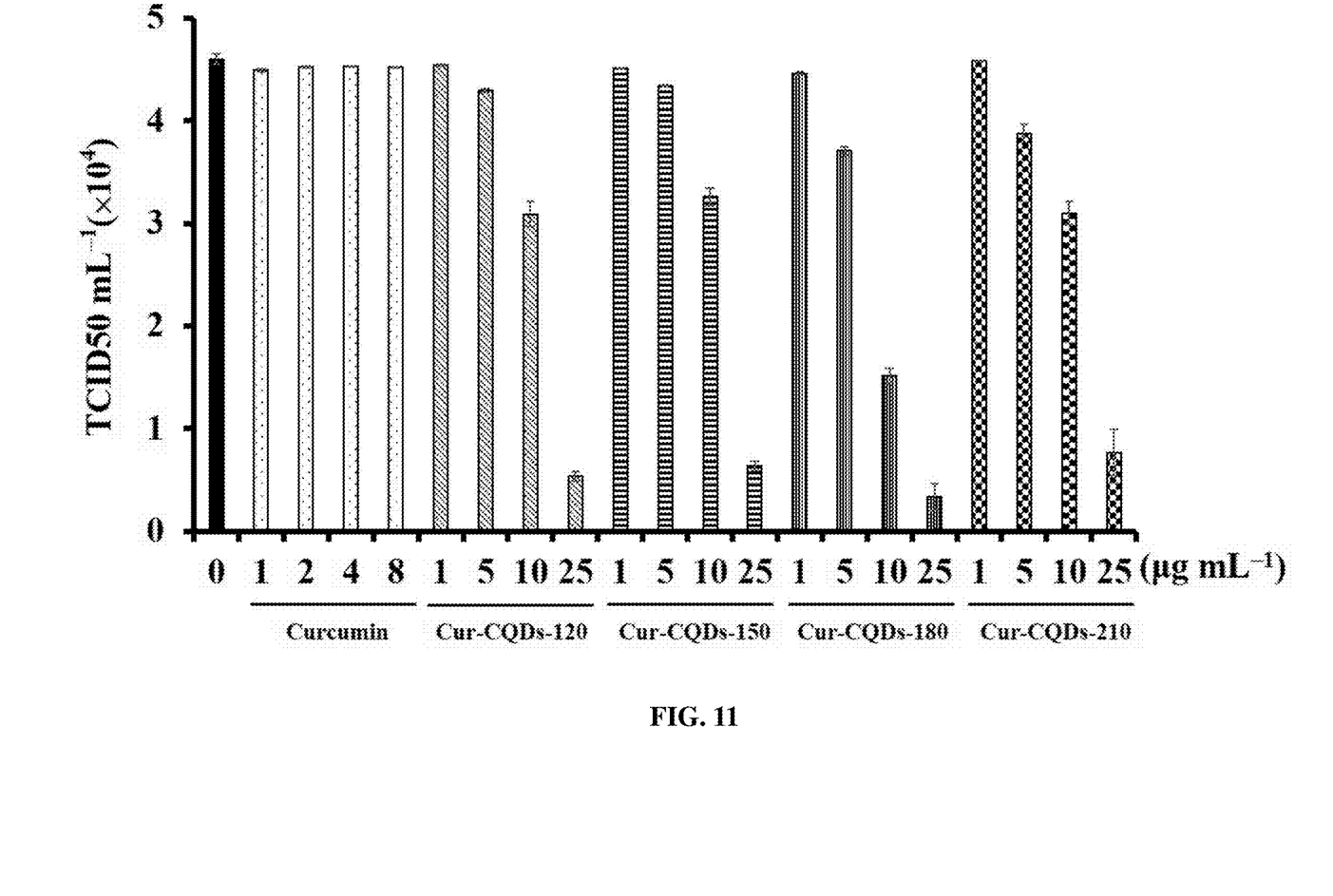
FIG. 11 shows the TCID50 of Cur-CQDs.

FIG. 11 shows the TCID50 of Cur-CQDs relveals the Cur-CQDs-180 better anti-viral capability.

IV. Cytotoxicity and Antiviral Activities of Cur-CQDs against EV71 in RD Cells

Table. 2 lists the summary results of cytotoxicity and antiviral activities of Cur-CQDs synthesized at 120, 150, 180 and 210° C. against EV71 infected RD cell.

TABLE 2

Cytotoxicity and antiviral
activities of the compounds against EV71 in RD cell.

| Compounds | Cytotoxicity | Antiviral activity | |
|---|---|---|---|
|  | $CC_{50}$ (µg $mL^{-1}$) | $EC_{50}$[a] (µg $mL^{-1}$) | SI[b] |
| Curcumin | >13.0 | >200.0 | 0.1 |
| Cur-CQDs-120 | 50.0 | 14.6 | 3.4 |
| Cur-CQDs-150 | 65.0 | 15.5 | 4.2 |

TABLE 2-continued

Cytotoxicity and antiviral activities of the compounds against EV71 in RD cell.

| Compounds | Cytotoxicity $CC_{50}$ (µg mL$^{-1}$) | Antiviral activity $EC_{50}{}^{a)}$ (µg mL$^{-1}$) | $SI^{b)}$ |
|---|---|---|---|
| Cur-CQDs-180 | 452.2 | 8.2 | 55.1 |
| Cur-CQDs-210 | 430.0 | 15.2 | 28.3 |

$^{a)}$The concentration at which the compound inhibition rate of CPE reaches halfway between the baseline and maximum.
$^{b)}$The SI (Selective index) value represents the ratio of $CC_{50}/EC_{50}{}^{a}$ for each compound.

In certain embodiments, the Cur-CQDs-180 has the best effect because it has the largest SI value ($CC_{50}/EC_{50}$).

V. Immunofluorescence Assay

RD cells were treated with Cur-CQDs premixed with EV71. At 6 hours post infection, the cells were fixed with 3.6% formaldehyde for 60 min and treated with PBST (0.2% Tween-20) for 15 min, then blocked with 2% bovine serum albumin for 1 hour, and subsequently incubated with an EV71 VP1 antibody overnight, followed by reaction with a goat anti-mouse antibody conjugated with Alexa fluor 488 for 1 hour. The cell nuclei were stained with DAPI. Fluorescence was recorded using a laser scanning confocal microscope. EV71 was stained green, and the nuclei were stained blue.

Figure 12:
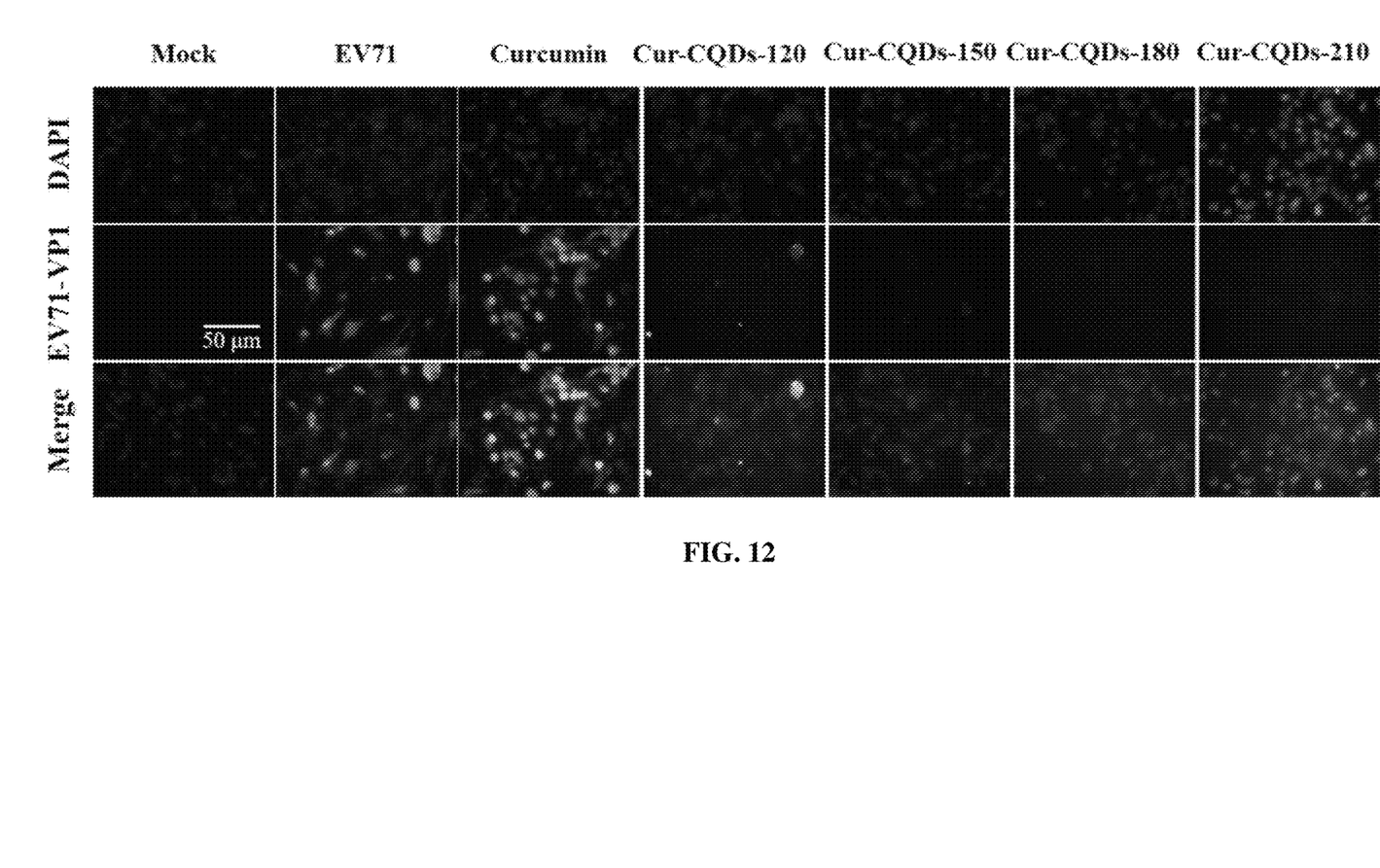
FIG. 12 shows the immunofluorescence assay of RD cells treated with Cur-CQDs premixed with EV71.

FIG. 12 shows the immunofluorescence assay of RD cells treated with CQDcurs premixed with EV71.

In certain embodiments, the Cur-CQDs-180 have the best effect on the basis of almost no green fluorescence (EV71-VP1) are observed.

Such syntheses, characterization, cytotoxicity and antiviral activities, and the related experiments are described in the previous reports (*Carbon* 2012, 12, 4738; *ACS Nano* 2017, 11, 6703; *Nanoscale* 2016, 8, 3040; *Antiviral Res.* 2017, 144, 311) incorporated herein by reference.

The invention includes embodiments in which exactly one member of the group is present in, employed in, or otherwise relevant to a given product or process. The invention also includes embodiments in which more than one, or all of the group members are present in, employed in, or otherwise relevant to a given product or process.

Those skilled in the art will recognize, or be able to ascertain by using no more than routine experimentation, many equivalents to the specific embodiments of the invention which is described herein. The scope of the present invention is not intending to be limited to the particular embodiments disclosed, but rather includes all embodiments falling within the scope of the appended claim. In addition, many modifications will be appreciated to adapt a particular instrument, situation or material to the teachings of the invention without departing from the essential scope thereof.

The invention claimed is:

1. A method of preparation of a curcumin nanoparticle comprising at least one curcumin carbon quantum dot, comprising the steps of:
   a) heating a curcumin powder at a temperature range from 120 to 210° C. to yield a residue;
   b) dissolving the residue with sodium phosphate buffer in a solution; and
   c) purifying the solution; and
   wherein the curcumin carbon quantum dot comprises (111) and (200) planes in an X-ray diffraction pattern.

2. The method of claim 1, wherein the temperature is 180° C.

3. The method of claim 1, further comprising the step of homogenizing the solution.

4. The method of claim 1, wherein the step of c) is performed in sodium chloride solution through a dialysis membrane.

5. An engineered curcumin nanoparticle prepared by the method of claim 1, comprising at least one curcumin carbon quantum dot.

6. The engineered curcumin nanoparticle of claim 5, wherein the curcumin carbon quantum dot is uniform, monodispersed sphere.

7. The engineered curcumin nanoparticle of claim 5, wherein the curcumin carbon quantum dot has a diameter of 3.2 to 8.5 nm.

8. An engineered curcumin nanoparticle comprising at least one curcumin carbon quantum dot, wherein the curcumin carbon quantum dot comprises at least one curcumin functional group on the surface, wherein the curcumin carbon quantum dot comprises (111) and (200) planes in an X-ray diffraction pattern.

9. The engineered curcumin nanoparticle of claim 8, wherein the curcumin functional group is selected from the group consisting of hydroxyl group, methoxy group and phenol group.

10. The engineered curcumin nanoparticle of claim 8, wherein the curcumin carbon quantum dot is uniform, monodispersed sphere.

11. The engineered curcumin nanoparticle of claim 8, wherein the curcumin carbon quantum dot has a diameter of 3.2 to 8.5 nm.

12. A composition having an antiviral activity comprising an effective amount of an engineered curcumin nanoparticle, wherein the engineered curcumin nanoparticle comprises at least one curcumin carbon quantum dot, wherein the curcumin carbon quantum dot comprises at least one curcumin functional group on the surface, wherein the curcumin carbon quantum dot comprises (111) and (200) planes in an X-ray diffraction pattern.

13. The composition of claim 12, wherein the curcumin functional group is selected from the group consisting of hydroxyl group, methoxy group and phenol group.

14. The composition of claim 12, wherein the curcumin carbon quantum dot is uniform, monodispersed sphere.

15. The composition of claim 12, wherein the curcumin carbon quantum dot has a diameter of 3.2 to 8.5 nm.

16. A method of preparing an antiviral composition, comprising the steps of:
   a) heating a curcumin powder at a temperature range from 120 to 210° C. to yield a residue;
   b) dissolving the residue with sodium phosphate buffer in a solution; and
   c) purifying the solution,
   wherein the antiviral composition comprises an effective amount of an engineered curcumin nanoparticle, and the engineered curcumin nanoparticle comprises at least one curcumin carbon quantum dot, and
   wherein the curcumin carbon quantum dot comprises (111) and (200) planes in an X-ray diffraction pattern.

17. The method of claim 16, wherein the temperature is 180° C.

18. The method of claim 16, further comprising the step of homogenizing the solution.

19. The method of claim 16, wherein the step of c) is performed in sodium chloride solution through a dialysis membrane.

20. A method for treatment of an infection, condition or disorder caused by a virus, comprising administering a therapeutically effective amount of an engineered curcumin nanoparticle composition, wherein the engineered curcumin nanoparticle composition comprises at least one curcumin carbon quantum dot, wherein the curcumin carbon quantum dot comprises at least one curcumin functional group on the surface, and wherein the curcumin carbon quantum dot comprises (111) and (200) planes in an X-ray diffraction pattern.

21. The method of claim 20, wherein the curcumin functional group is selected from the group consisting of hydroxyl group, methoxy group and phenol group.

22. The method of claim 20, wherein the virus is selected from the group consisting of Enterovirus.

23. The method of claim 20, wherein the curcumin carbon quantum dot is uniform, monodispersed sphere.

24. The method of claim 20, wherein the curcumin carbon quantum dot has a diameter of 3.2 to 8.5 nm.

* * * * *